(12) United States Patent
Golding

(10) Patent No.: US 8,530,651 B2
(45) Date of Patent: Sep. 10, 2013

(54) PROCESS FOR THE PREPARATION OF ANAGRELIDE AND ANALOGUES

(75) Inventor: Bernard Golding, Tyne (GB)

(73) Assignee: Shire LLC, Florence, KY (US)

( * ) Notice: Subject to any disclaimer, the term of this patent is extended or adjusted under 35 U.S.C. 154(b) by 167 days.

(21) Appl. No.: 13/132,001

(22) PCT Filed: Nov. 30, 2009

(86) PCT No.: PCT/GB2009/051621
§ 371 (c)(1),
(2), (4) Date: Jul. 7, 2011

(87) PCT Pub. No.: WO2010/070318
PCT Pub. Date: Jun. 24, 2010

(65) Prior Publication Data
US 2011/0263850 A1  Oct. 27, 2011

(30) Foreign Application Priority Data

Dec. 17, 2008  (GB) .................................. 0822970.0

(51) Int. Cl.
*C07D 487/04*  (2006.01)

(52) U.S. Cl.
USPC ........................................................ 544/250

(58) Field of Classification Search
USPC .......................................... 544/250; 560/22
See application file for complete search history.

(56) References Cited

U.S. PATENT DOCUMENTS

| 4,256,748 | A  | 3/1981  | Chodnekar |
| 5,801,245 | A  | 9/1998  | Lang |
| 6,388,073 | B1 | 5/2002  | Lang |
| 6,653,500 | B2 | 11/2003 | Lang |

FOREIGN PATENT DOCUMENTS

| WO | WO02/08228        | 1/2002 |
| WO | 2008/065444 A2    | 6/2008 |
| WO | WO 2008065445 A1 * | 6/2008 |
| WO | 2008/096145 A     | 8/2008 |

OTHER PUBLICATIONS

Kienzle F., et al: 7"1,5-Dihydroimidazoquinazolinones as Blood Platelet Aggregation Inhibitors", Chimie Therapeutique, Editions Dimeo, Arcueil, FR, vol. 17, No. 6, Jan. 1, 1982, pp. 547-556.
International Search Report and Written Opinion, European Patent Office, Feb. 8, 2010.
Written Opinion of the International Preliminary Examining Authority, European Patent Office, Nov. 23, 2010.
International Preliminary Report on Patentability, European Patent Office, Feb. 11, 2011.
"Structure-activity relationships of milrinone analogues determined in vitro in a rabbit heart membrane Ca(2+)-ATPase model." Cody V., J Med Chem. May 26, 1995;38(11):1990-7.
"Inhibitors of blood platelet cAMP phosphodiesterase. 2. Structure-activity relationships associated with 1,3-dihydro-2H-imidazo[4,5-b]quinolin-2-ones substituted with functionalized side chains." Meanwell NA., J Med Chem. Jul. 10, 1992;35(14):2672-87.

* cited by examiner

*Primary Examiner* — Kristin Vajda
(74) *Attorney, Agent, or Firm* — Lucas & Mercanti, LLP

(57) ABSTRACT

The present invention relates to a novel process for producing quinazoline compounds which are useful in therapy. More specifically, the compounds produced by the process of the invention are useful in the treatment of a number of cardiovascular diseases. The process of the invention provides 6,7-dichloro-1,5-dihydroimidazo[2,1-b]quinazolin 2(3H)-one, more commonly known as anagrelide and its analogues in a clean and efficient manner.

7 Claims, No Drawings

PROCESS FOR THE PREPARATION OF ANAGRELIDE AND ANALOGUES

CROSS-REFERENCE TO RELATED APPLICATION

This application is a 371 of PCT/GB2009/051621 filed on Nov. 30, 2009, which claims the benefit of British Patent Application No. 0822970.0 filed on Dec. 17, 2008, the contents of each of which are incorporated herein by reference.

The present invention relates to a novel process for producing quinazoline compounds which are useful in therapy. More specifically, the compounds are useful in the treatment of a number of cardiovascular diseases. More specifically, the invention relates to a process for producing 6,7-dichloro-1,5-dihydroimidazo[2,1-b]quinazolin 2 (3H)-one, more commonly known as anagrelide, and its analogues in a clean and efficient manner.

Anagrelide (6,7-dichloro-1,5-dihydroimidazo[2,1-b] quinazolin-2 (3H)-one, shown below as its hydrochloride salt, is a potent blood platelet reducing agent.

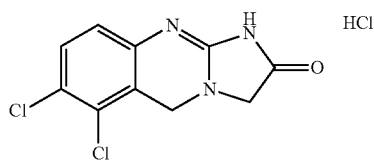 [SMILES: Cl ; O=C1CN2Cc3c(ccc(Cl)c3Cl)N=C2N1]

A number of US Patents have been issued on anagrelide and its method of making including U.S. Pat. Nos. 3,932,407; 4,146,718; 4,208,521; 4,357,330; Re 31,617; and 5,801,245. Published European patent applications EP 1373268, EP 1700840, EP 1700841, EP 1700842, EP 1700843, and EP 170859 also disclosed methods for preparing anagrelide.

Commercially, as discussed in U.S. Pat. No. 5,801,245, and as shown in FIG. 1, anagrelide has been prepared as the hydrochloride monohydrate (compound IV) from the intermediate, ethyl-N-(6-amino-2,3-dichlorobenzyl)glycine (compound I) either by reaction with cyanogen bromide in hot alcoholic solution, or, preferentially, by reaction with cyanogen bromide in an aprotic solvent such as toluene to give the iminoquinazoline intermediate (compound II), which is isolated and then reacted with a base in a hot solution of alcohol to form anagrelide base (compound III).

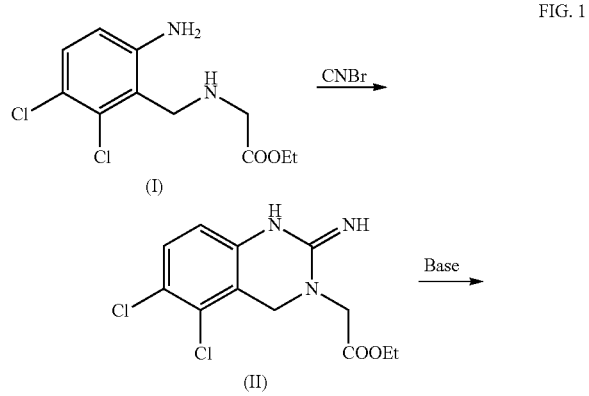

FIG. 1

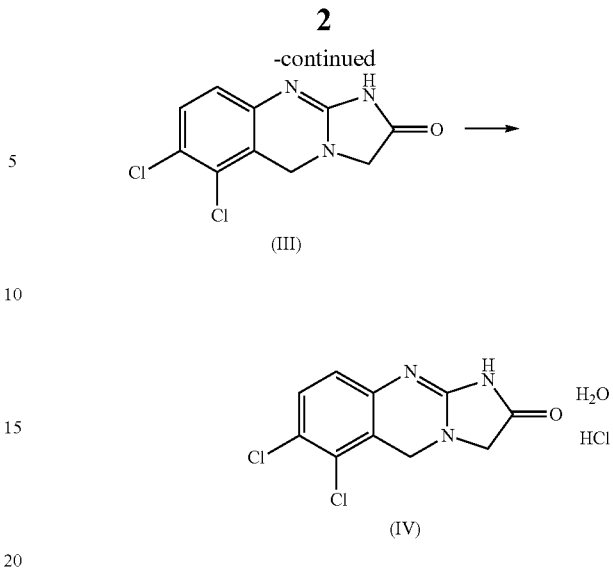

The hydrochloride monohydrate anagrelide salt (compound IV) is prepared by adding hydrochloric acid to a methanol slurry of anagrelide base (compound III) and heating to reflux. The hydrochloride salt is then hydrated in a high humidity chamber. These two steps are time-consuming however, and the yield of hydrochloride salt can be poor due to competing acid hydrolysis of the lactam ring and methyl ester formation. After 15 minutes at reflux, the isolated yield is 62% and this decreases to 40% after 2 hours.

Normally, salts are prepared when the free base has undesirable properties such as poor solubility or a non-solid physical state. In this case, both anagrelide base (compound III) and the hydrochloride salt (compound IV) are solids with low aqueous solubility. In addition, the water of crystallization can accelerate decomposition of the parent molecule through hydrolysis of the lactam ring and this presents long-term stability problems for pharmaceutical anagrelide formulations.

Radiolabeled anagrelide base has been used in pharmacokinetic studies in humans and monkeys and results show complete absorption into blood plasma demonstrating that the base is bioavailable. The free base is converted into the hydrochloride salt in the stomach to enhance absorption. Both the salt and the base exhibit equivalent pharmacological effects, and there is no inherent advantage to using the hydrochloride monohydrate salt as the active pharmaceutical agent.

As an important intermediate in the synthesis of anagrelide, ethyl-N-(6-amino-2,3-dichlorobenzyl) glycine (compound I) has been prepared from 2,3-dichloro-6-nitrobenzylamine (compound V) as shown in Figure 2. This material is no longer commercially readily available, however, as the precursor 2,3-dichloro-nitrobenzonitrile has extreme toxic and skin-irritant properties.

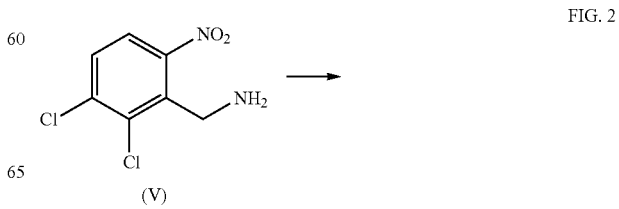

FIG. 2

-continued

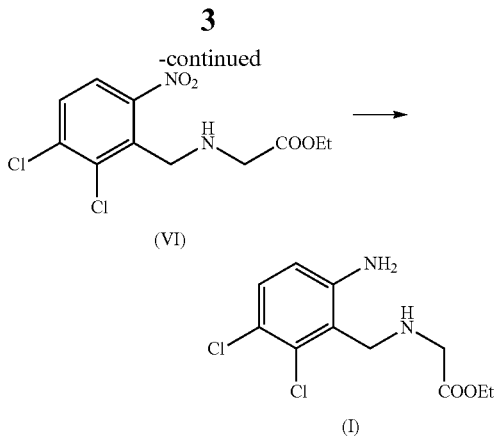

The conventional process for the formation of ethyl-N-(6-amino-2,3-dichlorobenzyl)glycine (compound I) from 1,2,3-trichlorobenzene is shown in U.S. Pat. No. 4,146,718.

An improved process for the formation of ethyl-N-(6-amino-2,3-dichlorobenzyl)glycine (compound I) using the intermediate 2,3-dichloro-6-nitrobenzyl halide (compound VIII), where halide is iodide, chloride or bromide, has been developed as an environmentally acceptable alternative (Figure 3). The route of preparation from 2,3-dichloro-6-nitrotoluene (compound VII) is described in U.S. Pat. No. 5,801,245, and involves a radical halogenation of the toluene group. Radical conditions can be nonselective, however, and could be difficult to effectively implement in large-scale commercial manufacture.

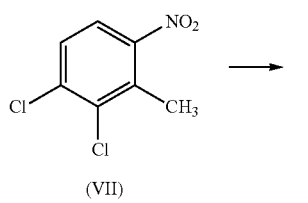

FIG. 3

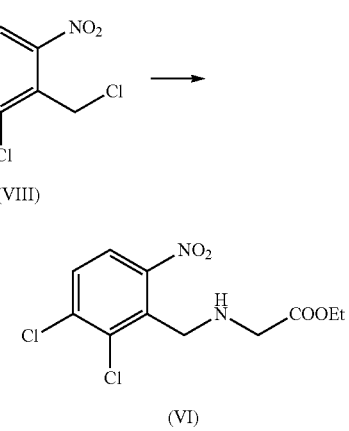

In both reactions shown in Figures 2 and 3, ethyl-N-(2,3-dichloro-6-nitrobenzyl)glycine (compound VI) is reduced to the 6-amino-2,3-dichlorobenzyl glycine (compound I) by stannous chloride reduction ($SnCl_2$/HCl). A disadvantage of this route is the formation of large amounts of tin-containing waste products. In addition, the strongly acidic reaction conditions can promote chlorination of the aromatic ring, producing a mixture of tri-chloro impurities which are difficult to remove in successive steps.

A further problem with the prior art process is that a number of synthetic steps are required to produce the quinazoline compounds in the disclosed processes, with each synthetic step leading both to a reduction in yield and increasing the possibility of competing side reactions. Thus the conventional routes require effort to purify the intermediate and final products and may not give an optimal yield. Work up and purification may thus be needed after one or more of the intervening steps and final purification is always required.

Bearing in mind the problems and deficiencies of the prior art, it is therefore an object of the present invention to provide an improved synthetic process for the making of anagrelide whether in base or salt form.

It is an aim of the present invention to provide a synthetically efficient process for the production of quinazoline derivatives which avoids the problems of the prior art processes. It is also an aim to provide a process in which the convergency (i.e. the bringing together of synthetic fragments) is maximised. It is a further aim to ensure that the need for purification and workup is minimised. It is a particular aim of the present invention to provide a process which minimizes the need for intermediate and final purification steps. It is thus an aim to provide a route to the compounds of formula (I) which offers an improved yield relative to the existing routes. It is a further aim of the process of the present invention to avoid the use of tin compounds, where possible, on account of their hazardous nature and troublesome by-products.

It is an additional aim of the present invention to make suitable intermediates from readily available starting materials. Ideally this is achieved by an environmentally acceptable method.

Still further objects and advantages of the present invention will become apparent from the details provided in the specification.

We have found an improved route to the quinazoline derivatives of formula (I) above via certain novel intermediates. The present invention thus satisfies some or all of the above aims. This is achieved by using a process involving a nitrobenzylsulfonate as an intermediate.

According to a first aspect of the present invention there is provided a method for making a compound of Formula (IX):

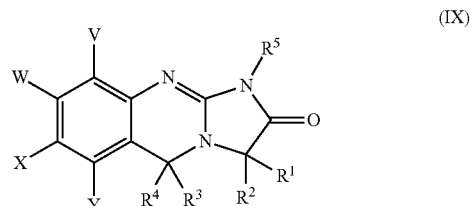

wherein:

$R^1$ and $R^2$ independently represent hydrogen or a blocking group which functions to directly or indirectly prevent metabolic reaction at the 3-position of substitution;

$R^3$ and $R^4$ are hydrogen;

V, W, X, and Y, are independently chosen from the group comprising: H, F, Cl, I, Br, CN, $C_{1-6}$ alkyl, $C_{1-6}$ haloalkyl, $C_{1-6}$ alkoxy, $C_{1-6}$ haloalkoxy and $C_{1-6}$ alkanoyl; and $R^5$ is H, $C_{1-6}$ alkyl or OH;

comprising the steps: (a) nitrating a compound of formula (X):

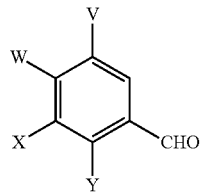

to form a compound of formula (XI):

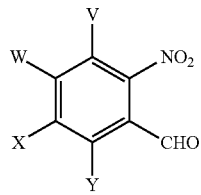

(b) reacting the compound of formula (XI) under reducing conditions to form a compound of formula (XII):

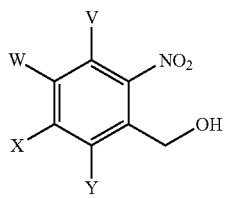

(c) reacting the compound of formula (XII) with an alkyl- or aryl-sulfonyl halide of formula $R^6SO_2T$ and an organic base to form a compound of formula (XIII):

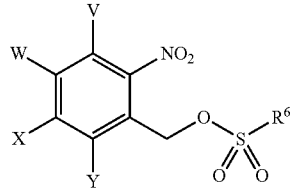

wherein;

$R^6$ is an optionally substituted $C_{1-6}$ alkyl group or an optionally substituted aryl group, each of which can be optionally substituted where chemically possible by 1 to 3 substituents independently selected from the group comprising: $C_{1-6}$alkyl, $C_{1-6}$ haloalkyl, —$SR^8$, —$OR^9$, —$NR^8R^9$, —$NO_2$, $SCF_3$, halogen, —$C(O)R^8$, —CN, and —$CF_3$, where $R^8$ and $R^9$ are independently H or $C_{1-6}$ alkyl; and T is halo;

(d) reacting the compound of formula (XIII) with an organic base and a glycine derivative of formula (XIV)

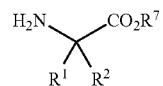

wherein $R^7$ is an optionally substituted $C_{1-6}$ alkyl group or aryl group, each of which can be optionally substituted by 1 to 3 substituents independently selected from the group comprising: $C_{1-6}$alkyl, $C_{1-6}$haloalkyl, —$SR^8$, —$OR^9$, —$NR^8R^9$, —$NO_2$, $SCF_3$, halogen, —$C(O)R^8$, —CN, and —$CF_3$, where $R^8$ and $R^9$ are independently H or $C_{1-6}$ alkyl, to form a compound of formula (XV):

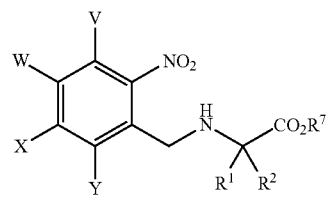

(e) reacting the compound of formula (XV) under reducing conditions to form a compound of formula (XVI):

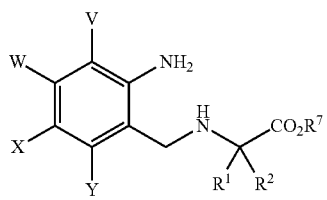

(f) reacting the compound of formula (XVI) under bromocyanation conditions to form a compound of formula (XVII):

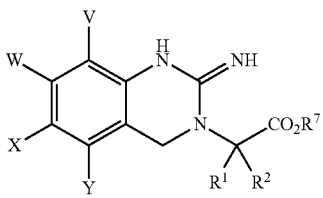

(g) reacting the compound of formula (XVII) under cycloalkylation conditions to form the compound of formula (IX):

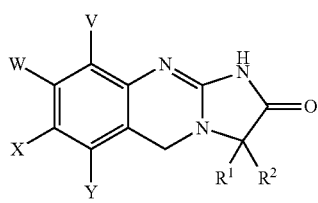

According to a second aspect of the present invention there is provided a method for making a compound of formula (XIII):

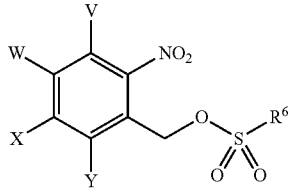

by reacting the compound of formula (XII)

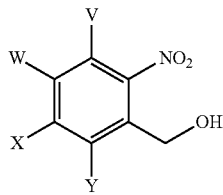

with an alkyl- or aryl-sulfonyl halide of formula $R^6SO_2T$ and an organic base, wherein:

V, W, X, and Y, are independently chosen from the group comprising: H, F, Cl, I, Br, CN, $C_{1-6}$ alkyl, $C_{1-6}$ haloalkyl, $C_{1-6}$ alkoxy, $C_{1-6}$ haloalkoxy and $C_{1-6}$ alkanoyl;

$R^6$ is an optionally substituted $C_{1-6}$ alkyl group or an optionally substituted aryl group, each of which can be optionally substituted where chemically possible by 1 to 3 substituents independently selected from the group comprising: $C_{1-6}$alkyl, $C_{1-6}$ haloalkyl, $-SR^8$, $-OR^9$, $-NR^8R^9$, $-NO_2$, $SCF_3$, halogen, $-C(O)R^8$, $-CN$, and $-CF_3$, where $R^8$ and $R^9$ are independently H or $C_{1-6}$ alkyl; and T is halo.

In an embodiment, the alkyl or aryl-sulfonyl halide is a chloride. However, it is possible to use alternative halo derivatives, eg a sulfonyl fluoride.

In another embodiment, the anhydride equivalent of $R^6SO_2T$, a compound of formula $(R^6SO_2)_2O$ could be used instead to prepare the nitrobenzylsulfonate of formula (XIII). The anhydride may be a symmetrical anhydride or a mixed anhydride in which each $R^6$ is different.

According to a third aspect of the present invention there is provided a method for making a compound of formula (XV):

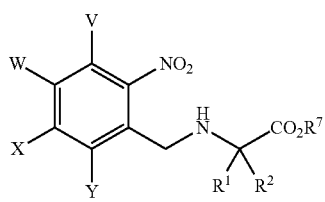

by reacting the compound of formula (XIII)

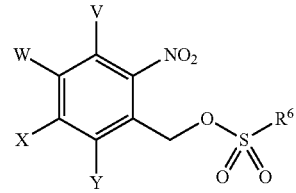

with an organic base and a glycine derivative of formula (XIV)

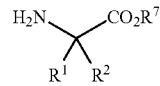

to form the compound of formula (XV), wherein:

V, W, X, and Y, are independently chosen from the group comprising: H, F, Cl, I, Br, CN, $C_{1-6}$ alkyl, $C_{1-6}$ haloalkyl, $C_{1-6}$ alkoxy, $C_{1-6}$ haloalkoxy and $C_{1-6}$ alkanoyl; and $R^1$ and $R^2$ are independently selected from the group comprising: H; cyano; $C_{1-6}$ alkyl, $SC_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulfonyl and COOH; $C_{1-6}$ hydroxyalkyl; $C_{1-6}$ carboxyalkyl; and sulphide;

or $R^1$ and $R^2$ together with the carbon to which they are attached form a $C_{3-8}$ carbocyclic ring which may be optionally substituted by 1 to 5 groups chosen independently from the group comprising: halo, hydroxyl, cyano, nitro, $C_{1-4}$ haloalkyl, $C_{1-4}$ alkylsulfonyl and COOH;

or $R^1$ and $R^2$ together with the carbon atom to which they are attached represent a $C_{2-6}$ alkenyl or $C_{2-6}$ alkynyl group bound through a double bond to the ring to which it is attached and which may be optionally substituted by one to three groups independently selected from the group comprising: halo, hydroxyl, cyano, $C_{1-4}$ haloalkyl and COOH; and $R^7$ is an optionally substituted $C_{1-6}$ alkyl group or aryl group, each of which can be optionally substituted by 1 to 3 substituents independently selected from the group comprising: $C_{1-6}$alkyl, $C_{1-6}$haloalkyl, $-SR^8$, $-OR^9$, $-NR^8R^9$, $-NO_2$, $SCF_3$, halogen, $-C(O)R^8$, $-CN$, and $-CF_3$, where $R^8$ and $R^9$ are independently H or $C_{1-6}$ alkyl.

According to a fourth aspect of the present invention there is provided a compound of formula (XIII):

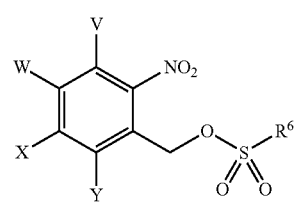

wherein V, W, X, Y, and $R^6$ are as previously defined above.

The following are embodiments of the invention which are relevant to each of the first, second, third and fourth aspects of the invention.

In an embodiment, Y is preferably halo, and is more preferably chloro.

In an embodiment, X is preferably halo, and is more preferably chloro.

In an embodiment, V is H.

In an embodiment, W is H.

In an embodiment, $R^1$ is H or an optionally substituted $C_{1-4}$ alkyl or $C_{3-8}$ cycloalkyl group.

In an embodiment, $R^2$ is H or an optionally substituted $C_{1-4}$ alkyl group or $C_{3-8}$ cycloalkyl.

In an embodiment, $R^1$ and $R^2$ are both methyl or together form a cyclopropyl group.

In each of the above embodiments for $R^1$ and $R^2$, one or more hydrogen atoms may be replaced by deuterium. Similarly, one or more carbon atoms may be replaced by $^{13}C$.

In an embodiment, $R^3$ is hydrogen or deuterium. Preferably, $R^3$ is hydrogen.

In an embodiment $R^4$ is hydrogen or deuterium. Preferably, $R^4$ is hydrogen.

In an embodiment, $R^5$ is hydrogen or deuterium. Preferably, $R^5$ is hydrogen.

In an embodiment, $R^6$ is an optionally substituted $C_{1-6}$ alkyl group or an optionally substituted aryl group. When $R^6$ is aryl it is preferably phenyl. More preferably $R^6$ is methyl or tolyl. Most preferably $R^6$ is methyl.

In an embodiment, $R^7$ is an optionally substituted $C_{1-6}$ alkyl group, and more preferably it is methyl or ethyl.

In an embodiment, T is chloro, fluoro or bromo. Preferably, T is chloro.

The reduction of compound (XI) to compound (XII) may be effected using a complex metal hydride. A suitable reducing agent is sodium borohydride.

In an embodiment, the organic base used to prepare the compound of formula (XIII) is an aliphatic or aromatic amine. Preferably the base is an aliphatic amine. More preferably the base is a tertiary aliphatic amine. Particularly suitable bases are tri ($C_{1-10}$ alkyl) amines such as triethylamine.

In an embodiment, the solvent used in the preparation of the compound of the formula (XIII) is a polar aprotic solvent. Suitable polar aprotic amendments include: dichloromethane, tetrahydrofuran, dimethylformamide, dimethyl sulfoxide, dialkyl ethers e.g. dimethyl ether, diethyl ether and glycols such as ethylene glycol. Preferably the solvent is dichloromethane.

In an embodiment, the process for forming the compound of formula (XIII) is carried out below room temperature (25° C.). More preferably the process is carried out at a temperature between −10° C. and +15° C., and most preferably between 0° C. and +10° C. The reaction is preferably conducted over a period of from 10 to 60 minutes and preferably about 30 minutes.

In a further embodiment, the resulting product of the reaction (which is the compound of the formula (XIII)) is isolated. Preferably it is used in the next step to form the compound of the formula (XV) without the need for chromatographic purification or recrystallisation.

In another embodiment, the organic base used in the process for forming the compound of formula (XV) is an aliphatic or aromatic amine. The base may be the same or different from that used to form the compound of formula (XIII). Preferably, the base is a tertiary aliphatic amine. Particularly suitable bases are tri ($C_{1-10}$ alkyl) amines such as triethylamine.

The process for forming the compound of formula (XV) preferably uses a polar aprotic solvent. The same solvents may be used as described in relation to the formation of the compound of formula (XIII) except for those with a boiling point of less than 70° C. It is preferred that the solvent has a higher boiling point i.e. greater than 70° C. Dimethylformamide is a particularly preferred solvent.

HBr is added to the reaction mixture after addition of the organic base in order to complete the reaction to form the compound of formula (XV). The resulting product is thus a hydrobromide salt. Equally, HCl could be used. Other acids such as sulfonic acids, eg methanesulfonic acid could also be used.

In an embodiment, the reaction is performed at elevated temperature i.e. above room temperature (25° C.). More preferably, the reaction is carried out at a temperature between 70° C. and 130° C., and most preferably at between 80° C. and 100° C.

In an embodiment, the compound of formula (XV) is reduced to a compound of formula (XVI) using a catalytic hydrogenation process. The catalyst may be a transition metal. The reaction may be carried out under homogeneous or heterogeneous conditions. Phase transfer catalysis may also be used. A preferred catalyst is Pd/C.

The present invention includes the synthesis of all pharmaceutically acceptable isotopically-labelled compounds of formulae (IX) to (XVII) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, ($^2H$ and $^3H$), carbon, ($^{11}C$, $^{13}C$ and $^{14}C$), chlorine, ($^{36}Cl$), fluorine, ($^{18}F$), iodine, ($^{123}I$ and $^{125}I$), nitrogen, ($^{13}N$ and $^{15}N$), oxygen, ($^{15}O$, $^{17}O$ and $^{18}O$), phosphorus, ($^{32}P$), and sulphur, ($^{35}S$).

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Figure 4 shows schematically how the process is applied to anagrelide itself. Surprisingly, 2,3-dichlorobenzaldehyde (compound XVIII) is nitrated preferentially at the 6-position to form 2,3-dichloro-6-nitrobenzaldehyde (compound XIX), separated from its isomers, and reduced to 2,3-dichloro-6-nitrobenzyl alcohol (compound XX) under standard reducing conditions. The preferential nitration at the 6-position was contrary to initial expectations in view of the known directing effects of the existing substituents. Benzaldehyde is known to produce the meta (3-nitro) product as the majority isomer in approximately 72% yield with the ortho isomer comprising only 19%. The nitrating agent is fuming nitric acid in concentrated sulfuric acid. This nitration procedure to produce the desired isomer as the majority product and the subsequent easy separation, which can be achieved by crystallisation as well as by chromatography, thus forms another novel aspect of the present invention. Treatment of the alcohol with an alkyl- or aryl-sulfonyl halide gives a 2,3-dichloro-6-nitrobenzylsulfonate derivative (compound XXI).

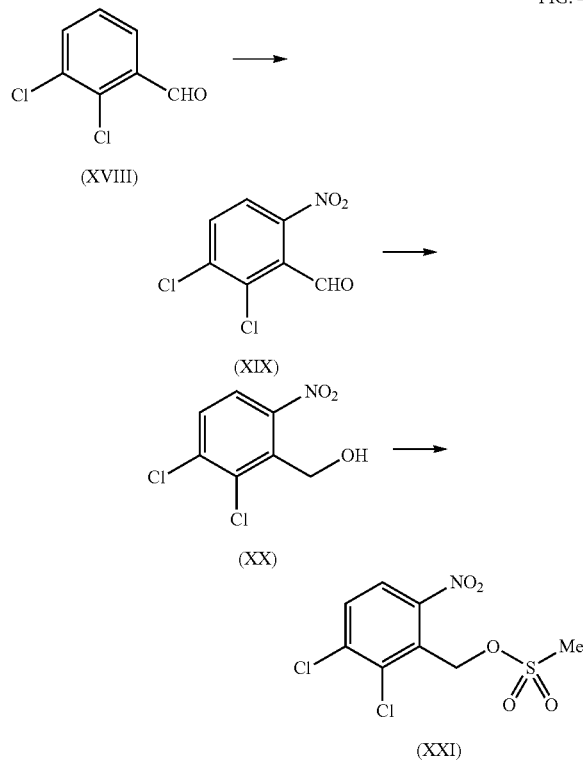

FIG. 4

Another useful feature of the process of the invention for the preparation of anagrelide or anagrelide derivatives is the discovery that the final cyclization reaction as shown for example in Figure 1 to form 6,7-dichloro-1,5-dihydroimidazo[2,1-b]quinazoline-2 (3H) one (compound III) from 5,6-dichloro-3,4-dihydro-2(1H)iminoquinazoline-3-acetate HBR (compound II) can be achieved at room temperature by addition of an organic base such as triethylamine (TEA), pyridine, or trimethylamine, preferably TEA, to a suspension of the starting material in water. Anagrelide base is obtained in about 99.8% purity by HPLC. The preparation of anagrelide base from ethyl 5,6-dichloro-3,4-dihydro-2 (1H) iminoquinazoline-3-acetate in the form of the hydrobromide (compound II) is conventionally achieved by cyclisation in refluxing organic alcohols in the presence of a base followed by treatment of anagrelide base with hydrogen bromide.

This leads to occlusion of residual solvents or organic impurities in the final product. Due to the low solubility of anagrelide free base in most organic solvents, further purification at this stage is limited. Since the iminoquinazoline intermediate 5,6-dichloro-3,4-dihydro-2(1H)iminoquinazoline-3-acetate hydrobromide (compound II) is insoluble in water at room temperature, the discovery that this media affords much purer anagrelide base (compound III) is surprising.

This finding also maintains the earlier process benefits, such as improved purity and avoidance of the need for extensive purification procedures, which are obtained by using the novel sulfonate intermediate at an earlier stage of the synthesis.

The formation of the anagrelide hydrochloride salt in refluxing methanol/hydrochloric acid exerts a powerful purification effect, readily removing the organic and solvent impurities. However, at reflux conditions, acid hydrolysis is fast and the yield of hydrochloride salt decreases rapidly over time.

With the larger batch sizes needed for commercial manufacture, the time the reaction mixture spends at reflux is significant. Thus, formation of the hydrochloride salt is a less efficient means of purification than preparing anagrelide base (compound III) in high purity using the method of the invention.

Figure 5 shows schematically how the process of the invention may be applied to the synthesis of 3,3-dimethyl anagrelide. The conditions described in each of the individual steps may be applied in general terms to other analogous transformations in the preparation of analogous substituted or unsubstituted anagrelides.

FIG. 5

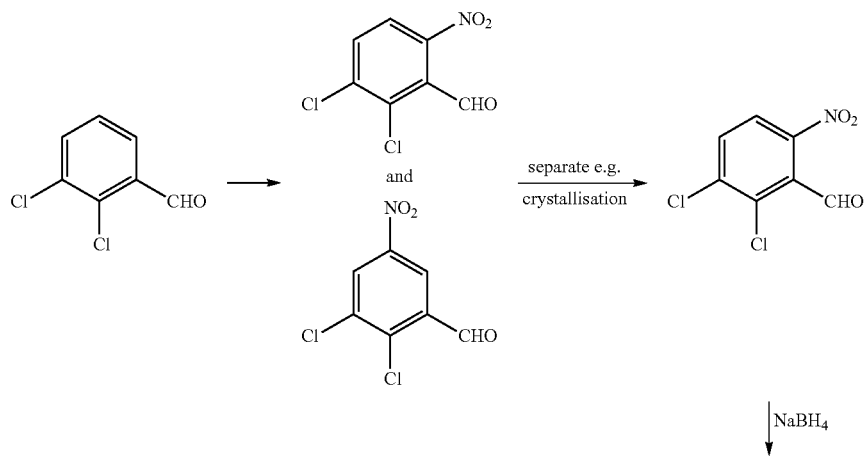

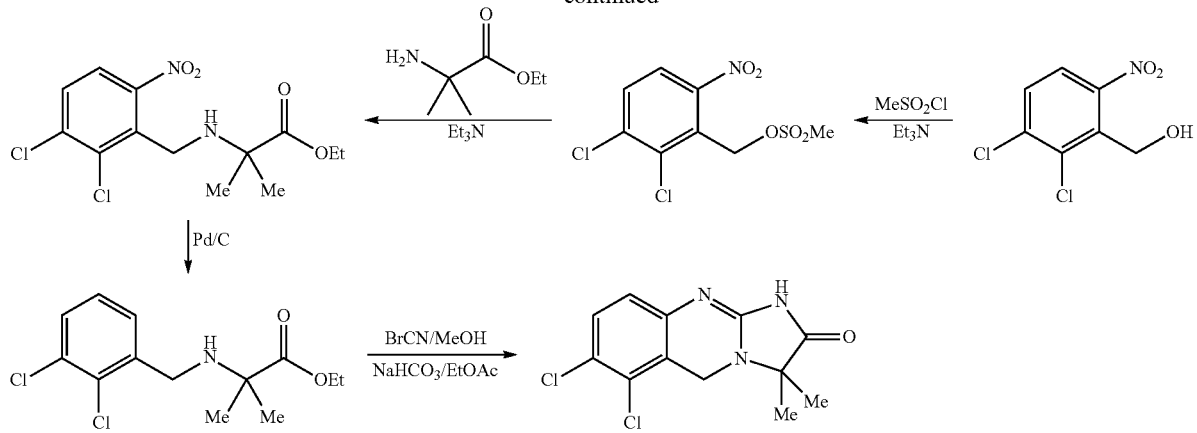

The skilled person will appreciate that adaptation of the methods herein described and/or adaptation of methods known in the art could be applied to the processes of the present invention.

For example, the skilled person will be immediately familiar with standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (6th edition (2007) or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide. Procedures for conducting standard synthetic transformations may also be found at www.orgsyn.org.

Referring to Figure 4, the 2,3-dichlorobenzaldehyde (compound XVIII) is surprisingly nitrated preferentially at the 6-position to form 2,3-dichloro-6-nitrobenzaldehyde (compound XIX) as discussed previously, separated from its isomer, and reduced to 2,3-dichloro-6-nitrobenzyl alcohol (compound XX) under standard reducing conditions. Separation of the nitro isomers can be conveniently effected by crystallisation because of the preferential formation of the desired 6-nitro derivative. This represents a significant processing advantage.

The nitration of 2,3-dichlorobenzaldehyde (compound XVIII) to form 2,3 dichloro-6-nitro benzaldehyde (compound XIX) is performed preferably by adding concentrated nitric acid to a solution of compound (XVIII) in sulfuric acid using an ice bath to maintain a reaction temperature of about −10 to 40° C., preferably 20 to 25° C.

The reaction mixture is generally stirred at this temperature for one hour or more and then preferably suspended in water and filtered. The filter cake is preferably washed with water to give a mixture of the compound XIX and its isomer 5-nitrobenzaldehyde. The isomers may be separated using an organic solvent such as hexane until the 5-nitro isomer is removed.

To form 2,3-dichloro-6-nitrobenzylalcohol (compound XX) from 2,3-dichloro-6-nitro benzaldehyde (compound XIX), compound XIX is preferably solubilized in a solvent or solvent mixture such as toluene and methanol. The solution of compound XIX is added to a reducing solution such as sodium borohydride in an organic solvent over a period of time to maintain a reaction temperature below about 40° C., preferably 25° C. The reaction is preferably stirred for 24 hours at room temperature under nitrogen and then washed with water. After removing the aqueous layer the organic layer is azeotropically dried and concentrated forming 2,3-dichloro-6-nitrobenzylalcohol (compound XX).

The sulfonic acid derivative is formed by reacting the alcohol in solution with an organic base with an alkyl- or arylsulfonyl halide or anydride, such as methanesulfonyl chloride, which is added to the solution maintained at below room temperature, e.g. preferably in the range 0 to 10 degrees.

The reaction is thus performed by first reacting 2,3-dichloro-6-nitrobenzyl alcohol (compound XX) and a base such as triethylamine in a suitable solvent under an inert atmosphere such as nitrogen with an alkyl- or aryl-sulfonyl halide such as methanesulfonyl chloride, or an anhydride such as methanesulfonic anhydride.

In a subsequent step, which is also part of the present invention, the resulting sulfonate derivative is taken up in a suitable solvent and treated with triethylamine and the relevant glycine derivative. The sulfonate derivative may be isolated or carried forward into the next step without isolation. In the case of preparing 3,3-dimethylanagrelide, for example, the resulting glycine derivative is the 1,1-dimethylethyl N-(2,3-dichloro-6-nitrobenzyl)glycine derivative (compound XXII):

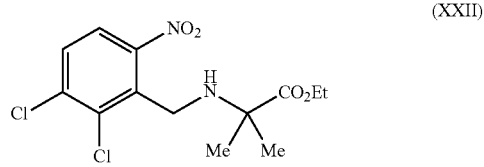 [SMILES: CCOC(=O)C(C)(C)NCc1c([N+](=O)[O-])ccc(Cl)c1Cl]

(XXII)

One benefit of the present invention is that 1,1-dimethylethyl N-(2,3-dichloro-6-nitrobenzyl)glycine derivative (compound XXII) and its 1-unsubstituted or substituted analogues can be formed directly from the corresponding 2,3-dichloro-6-nitrobenzyl alcohol (compound XX) without the need to form an intermediate halo derivative such as those described in the prior art. This fact leads to a number of unexpected advantages both in this particular step and in the overall synthesis.

The aromatic nitro group on the glycine derivative is then reduced by a conventional reducing agent such as a mixture of stannous chloride and hydrochloric acid or by other reducing agents as discussed below. In one procedure according to the invention, a solution of the glycine (compound XXII) is slowly added to the tin chloride solution and the resulting reaction mixture heated at an elevated temperature of about 40-50° C. for about two hours. Solids are filtered and the filtered cake dissolved in water and an organic solvent such as methylene chloride. The pH of the solution is adjusted to about 12.5 with sodium hydroxide and the organic phase separated and the aqueous phase extracted with methylene chloride. The combined organic phases are washed with water and dried azeotropically and the solution is concentrated, an organic solvent added and the solution cooled to −20 to −30° C. The precipitated solids are collected by filtration and the crude product is recrystallized from heptane or another organic solvent.

Where possible, the invention seeks to avoid the use of a tin-reagent to effect the reduction. Thus in another procedure according to the invention, 1,1-dimethyl-ethyl N-(2,3-dichloro-6-nitrobenzyl)glycine (compound XXII) may also be catalytically hydrogenated using a metal or metal-based catalyst such as platinum, platinum oxide, rhodium, and palladium on carbon under hydrogen pressure. The catalyst is then removed by filtration and the filtrate concentrated, diluted with water and an organic solvent and basified using an alkali to a pH of about 9-10. The organic phase is separated and concentrated and the crude material purified by low temperature recrystallization to give 1,1-dimethyl-ethyl-(6-amino-2,3-dichlorobenzyl)glycine.

The preparation of compound (II) from the glycine derivative of formula (I) is achieved using cyanogen bromide in a hot alcohol solution or by reaction of cyanogen bromide in an aprotic solvent.

6,7-dichloro-1,5-dihydroimidazo[2,1-b]quinazoline-2(3H)one (compound III) may be prepared from compound (II) by suspending 5,6-dichloro-3,4-dihydro 2(1H)iminoquinazoline-3-acetate HBr (compound (II)) in water and adding an organic base such as TEA. After filtering the solution the filtered cake is washed in water and the solids suspended in alcohol. After filtering, the solids are rinsed in an alcohol and dried to give compound (III).

For the case of 3,3-dimethylanagrelide in particular, the synthetic procedure of the invention can thus be illustrated schematically as follows in Figure 6:

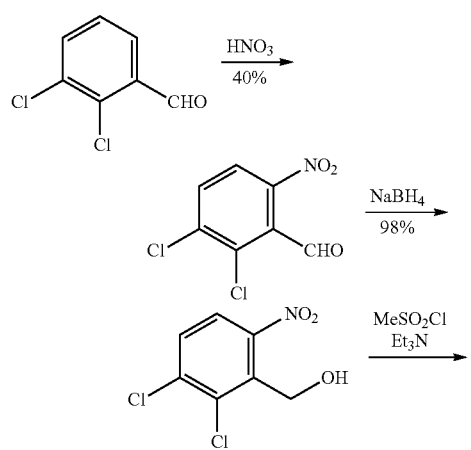

FIG. 6

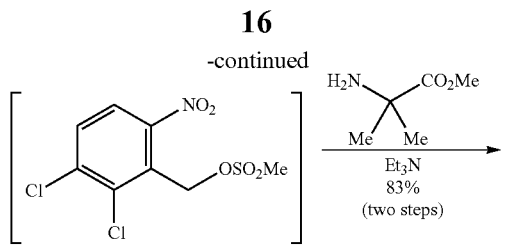

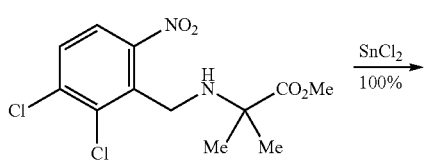

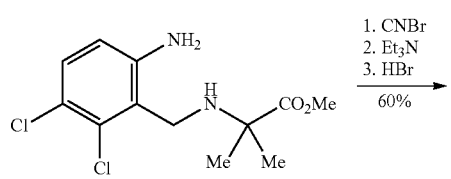

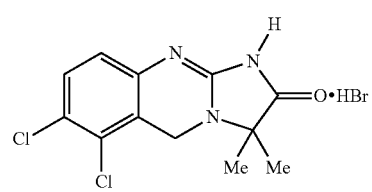

EXAMPLES 2,3-Dichloro-6-nitrobenzaldehyde

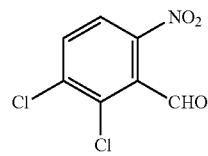 [SMILES: O=Cc1c([N+](=O)[O-])ccc(Cl)c1Cl]

To 2,3-dichlorobenzaldehyde (20 g, 114 mmol) in concentrated sulfuric acid (100 mL) was added cautiously fuming nitric acid (5.4 mL, 8.16 g, 130 mmol). The resulting solution was stirred for 1 hour, then poured onto an ice/water slurry and the precipitate collected by filtration. This was dissolved in diethyl ether (400 mL), and the solution washed with water and saturated sodium carbonate, then dried (MgSO$_4$) and concentrated. The residue was re-dissolved in the minimum amount of hot diethyl ether, then poured quickly into vigorously stirred petrol (1 L). After stirring for a further 10 minutes, the precipitate was collected by suction filtration and dried under vacuum to yield 2,3-dichloro-6-nitrobenzaldehyde, 9.98 g (40%), essentially free of isomers.

$R_f$ 0.32 (petrol-diethyl ether, 8:2 v/v)

$^1$H NMR (CDCl$_3$, 300 MHz): δ 10.34 (s, 1H, CHO), 8.01 (d, J=8.7 Hz, 1H, ArH), 7.76 (d, J=8.7 Hz, 1H, ArH).

2,3-Dichloro-6-nitrobenzyl alcohol

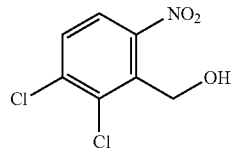 [SMILES: O=[N+]([O-])c1ccc(Cl)c(Cl)c1CO]

To a solution of 2,3-dichloro-6-nitrobenzaldehyde (7.62 g, 34.9 mmol) in tetrahydrofuran (75 mL) was added sodium borohydride (1.31 g, 34.9 mmol) followed by ethanol (1.75 mL), and the mixture was stirred for 1.5 hours. Saturated aqueous ammonium chloride (75 mL) was added, and the solution was extracted three times with EtOAc. The combined organic layers were dried (MgSO$_4$) and then concentrated to give 2,3-dichloro-6-nitrobenzyl alcohol, as an oil which crystallised, 7.62 g (98%).

R$_f$ 0.37 (petrol-diethyl ether, 8:2 v/v)
$^1$H NMR (CDCl$_3$, 300 MHz): δ 7.78 (d, J=8.9 Hz, 1H, ArH), 7.60 (d, J=8.9 Hz, 1H, ArH), 4.96 (s, 2H, benzylic CH$_2$), 2.77 (broad s, 1H, OH).

Methyl 2-aminoisobutyrate Hydrochloride

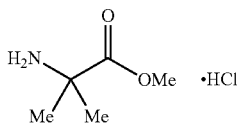

To a suspension of 2-aminoisobutyric acid (25.0 g, 243 mmol) in methanol (300 mL) was added thionyl chloride (27.0 mL, 43.0 g, 365 mmol) and the reaction was heated at reflux for 12 hours. The resulting solution was concentrated and triturated with diethyl ether-tetrahydrofuran to yield the product as a white powder, 29.8 g (80%).

$^1$H NMR (DMSO-d$_6$, 300 MHz): δ 8.80 (broad s, 3H, NH$_3^+$), 3.74 (s, 3H, CH$_3$O), 1.48 (s, 6H, 2×CH$_3$).

Methyl 1-[(2,3-dichloro-6-nitrobenzyl)amino]isobutyrate

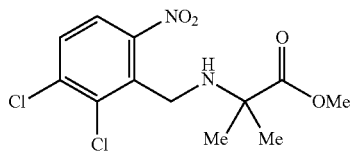

To a solution of 2,3-dichloro-6-nitrobenzyl alcohol (9.00 g, 40.5 mmol) and triethylamine (8.35 mL, 6.06 g, 60.0 mmol) in anhydrous dichloromethane (200 mL) under nitrogen at 5° C. was added methanesulfonyl chloride (3.48 mL, 5.15 g, 45.0 mmol) dropwise. The solution was stirred for 1 hour, then transferred to a separating funnel and washed sequentially with ice-cold 1M hydrochloric acid, saturated aqueous sodium carbonate and water, dried (MgSO$_4$) and concentrated to afford the mesylate as a waxy solid.

The mesylate was taken up in anhydrous DMF (200 mL) and treated with triethylamine (13.9 mL, 10.1 g, 100 mmol) and methyl-2-aminoisobutyrate hydrochloride (7.68 g, 50 mmol), and the mixture stirred and heated at 90° C. overnight. After cooling, the mixture was partitioned between water (500 mL) and diethyl ether (500 mL) and the layers separated. The aqueous layer was re-extracted with diethyl ether (2×200 mL) and the combined organic layers were washed with water (5×200 mL), dried (MgSO$_4$), filtered through a short pad of silica and concentrated to an oil which was used without further purification, 10.78 g (83%).

R$_f$ 0.49 (petrol-diethyl ether, 8:2 v/v)
$^1$H NMR (CDCl$_3$, 300 MHz): δ 7.65 (d, J=9.0 Hz, 1H, ArH), 7.51 (d, J=9.0 Hz, 1H, ArH), 3.98 (s, 2H, benzylic CH$_2$), 3.75 (s, 3H, CH$_3$O), 1.36 (s, 6H, 2×CH$_3$).

Methyl 1-[(6-amino-2,3-dichlorobenzyl)amino]isobutyrate

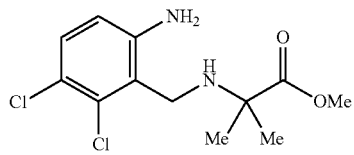 [SMILES: COC(=O)C(C)(C)NCc1c(N)ccc(Cl)c1Cl]

To a solution of methyl 1-[(2,3-dichloro-6-nitrobenzyl)amino]isobutyrate (10.70 g, 33.3 mmol) in ethanol (350 mL) was added SnCl$_2$.2H$_2$O (30.1 g, 133 mmol), and the resulting solution was heated at 55° C. for 3 hours. After cooling, the solution was poured into a rapidly-stirred mixture of saturated aqueous sodium carbonate (200 mL) and EtOAc (200 mL). After 5 minutes, Celite was added and the resulting slurry was filtered under vacuum through another slurry of Celite. The layers were separated and the aqueous was re-extracted with further EtOAc. The combined organic layers were dried (MgSO$_4$), filtered through a pad of silica, and concentrated to afford an oil which was used without further purification, quantitative yield.

$^1$H NMR (DMSO-d$_6$, 300 MHz): δ 7.18 (d, J=8.7 Hz, 1H, ArH), 6.63 (d, J=8.7 Hz, 1H, ArH), 3.69 (s, 2H, benzylic CH$_2$), 3.66 (s, 3H, CH$_3$O), 1.29 (s, 6H, 2×CH$_3$).

3,3-Dimethylanagrelide Hydrobromide

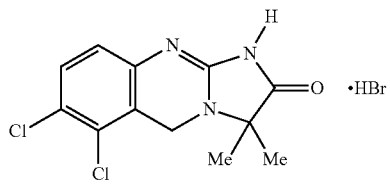 [SMILES: CC1(C)C(=O)NC2=Nc3ccc(Cl)c(Cl)c3CN21 ; Br]

To a solution of methyl 1-[(6-amino-2,3-dichlorobenzyl)amino]isobutyrate (8.73 g, 30.0 mmol) in toluene (120 mL) was added dropwise a solution of cyanogen bromide (3.44 g, 32.0 mmol) in toluene (30 mL). The resulting solution was stirred at room temperature for 1.5 hours, then at 100° C. for 1 hour and finally at room temperature overnight. The solvent was evaporated and the residue suspended in methanol (100 mL). Triethylamine (7.0 mL, 5.05 g, 50 mmol) was added and the resulting suspension was stirred for 1 hour. The mixture was centrifuged in portions to isolate the fine precipitate, which was washed twice with methanol by decantation and centrifugation. The resulting thick slurry was transferred to a flask and the solvent evaporated to afford 3,3-dimethylanagrelide free base. This was then suspended in fresh methanol (50 mL), treated with 48 wt % hydrobromic acid (2.0 mL, 3.0 g, 18 mmol), and the solution briefly heated to reflux. Charcoal (ca. 1 g) was added and the solution was filtered through Celite whilst still near to reflux temperature. After cooling, the methanol was evaporated and the residue was re-crystallised from refluxing ethanol (50 mL) to afford 3,3-dimethylanagrelide hydrobromide, as a white crystalline solid which was collected by suction filtration, washed with diethyl ether and dried under high vacuum at 70° C. overnight. Yield obtained (including further crops from mother liquors) 60% overall.

$^1$H NMR (DMSO-$d_6$, 300 MHz): δ 7.62 (d, J=9 Hz, 1H, ArH), 7.09 (d, J=9 Hz, 1H, ArH), 4.64 (s, 2H, benzylic CH$_2$), 1.43 (s, 6H, 2×CH$_3$).

The invention claimed is:

1. A method for making a compound of Formula (IX):

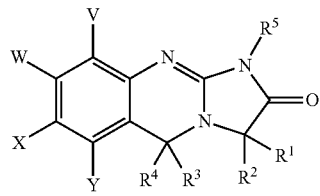

(IX)

wherein:
R$^1$ and R$^2$ are both methyl or together form a cyclopropyl group;
R$^3$ and R$^4$ are hydrogen;
V, W, X, and Y, are independently chosen from the group consisting of H, F, Cl, I, Br, CN, C$_{1-6}$ alkyl, C$_{1-6}$ haloalkyl, C$_{1-6}$ alkoxy, C$_{1-6}$ haloalkoxy and C$_{1-6}$ alkanoyl; and
R$^5$ is H, C$_{1-6}$ alkyl or OH;
comprising the steps: (a) nitrating a compound of formula (X):

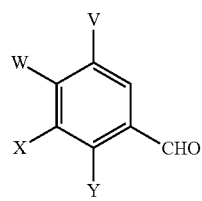

(X)

to form a compound of formula (XI):

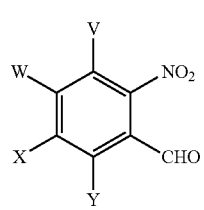

(XI)

(b) reacting the compound of formula (XI) under reducing conditions to form a compound of formula (XII):

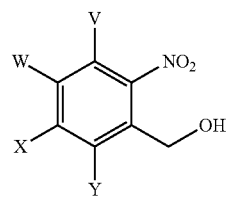

(XII)

(c) reacting the compound of formula (XII) with an alkyl- or aryl-sulfonyl halide of formula R$^6$SO$_2$T and an organic base to form a compound of formula (XIII):

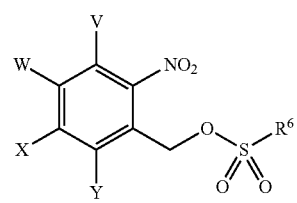

(XIII)

wherein:
R$^6$ is an optionally substituted C$_{1-6}$ alkyl group or an optionally substituted aryl group, each of which can be optionally substituted where chemically possible by 1 to 3 substituents independently selected from the group consisting of C$_{1-6}$alkyl, C$_{1-6}$ haloalkyl, —SR$^8$, —OR$^9$, —NR$^8$R$^9$, —NO$_2$, SCF$_3$, halogen, —C(O)R$^8$, —CN, and —CF$_3$, where R$^8$ and R$^9$ are independently H or C$_{1-6}$ alkyl; and T is halo;
(d) reacting the compound of formula (XIII) with an organic base and a glycine derivative of formula (XIV)

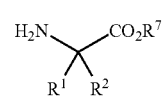

(XIV)

wherein R$^7$ is an optionally substituted C$_{1-6}$ alkyl group or aryl group, each of which can be optionally substituted by 1 to 3 substituents independently selected from the group consisting of C$_{1-6}$alkyl, C$_{1-6}$haloalkyl, —SR$^8$, —OR$^9$, —NR$^8$R$^9$, —NO$_2$, SCF$_3$, halogen, —C(O)R$^8$, —CN, and —CF$_3$, where R$^8$ and R$^9$ are independently H or C$_{1-6}$ alkyl;
to form a compound of formula (XV):

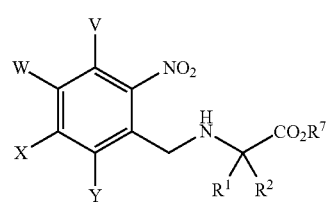

(XV)

(e) reacting the compound of formula (XV) under reducing conditions to form a compound of formula (XVI):

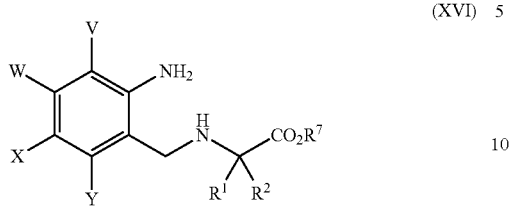

(XVI)

(f) reacting the compound of formula (XVI) under bromocyanation conditions to form a compound of formula (XVII):

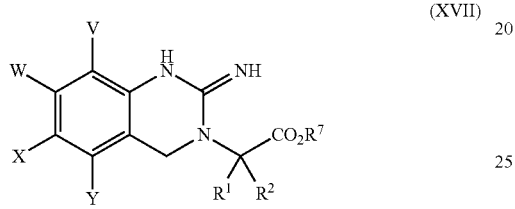

(XVII)

(g) reacting the compound of formula (XVII) under cycloalkylation conditions to form the compound of formula (IX):

(IX)

2. The method of claim 1, wherein Y is halo.
3. The method of claim 2, wherein Y is chloro.
4. The method of claim 1, wherein X is halo.
5. The method of claim 4, wherein X is chloro.
6. The method of claim 1, wherein V is H.
7. The method of claim 1, wherein W is H.

* * * * *

UNITED STATES PATENT AND TRADEMARK OFFICE
CERTIFICATE OF CORRECTION

PATENT NO. : 8,530,651 B2  Page 1 of 1
APPLICATION NO. : 13/132001
DATED : September 10, 2013
INVENTOR(S) : Bernard Golding It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this

Fifteenth Day of September, 2015

Michelle K. Lee
*Director of the United States Patent and Trademark Office*